US012797187B2

(12) United States Patent
Anderson et al.

(10) Patent No.: US 12,797,187 B2
(45) Date of Patent: Nov. 17, 2026

(54) TYNE DOCKING FOR PERCUTANEOUS CORONARY INTERVENTION ACCESS

(71) Applicant: Medtronic Vascular, Inc., Santa Rosa, CA (US)

(72) Inventors: Marc A. Anderson, Galway (IE); Stephen Montgomery, Galway (IE); Michael J. Donegan, Galway (IE); Emma Keane, Galway (IE); David Killeen, Cork (IE); Shane Nolan, Clare (IE); Frank White, Galway (IE); Raymond Ryan, Limerick (IE)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 749 days.

(21) Appl. No.: 17/911,860

(22) PCT Filed: Mar. 23, 2021

(86) PCT No.: PCT/US2021/023554

§ 371 (c)(1),
(2) Date: Sep. 15, 2022

(87) PCT Pub. No.: WO2021/195005

PCT Pub. Date: Sep. 30, 2021

(65) Prior Publication Data

US 2023/0030295 A1 Feb. 2, 2023

Related U.S. Application Data

(60) Provisional application No. 62/993,383, filed on Mar. 23, 2020.

(51) Int. Cl.
*A61F 2/24* (2006.01)
*A61F 2/95* (2013.01)

(52) U.S. Cl.
CPC .............. *A61F 2/24* (2013.01); *A61F 2/2436* (2013.01); *A61F 2002/9528* (2013.01); *A61F 2220/0083* (2013.01)

(58) Field of Classification Search
CPC ...... A61F 2002/9528; A61F 2002/9511; A61F 2/2436; A61M 2025/0081;
(Continued)

(56) References Cited

U.S. PATENT DOCUMENTS 5,474,563 A * 12/1995 Myler ........................ A61F 2/95 606/108
5,683,451 A * 11/1997 Lenker .................... A61F 2/954 606/198
(Continued)

FOREIGN PATENT DOCUMENTS

EP 829242 A1 * 3/1998 ............... A61F 2/95
EP 1097728 A1 * 5/2001 ...... A61F 2002/9511
(Continued)

OTHER PUBLICATIONS

Translation of EP 829242 (Year: 1998).*
International Search Report and Written Opinion dated Jun. 29, 2021 in International Application No. PCT/US2021/023554.

*Primary Examiner* — Brian E Pellegrino
(74) *Attorney, Agent, or Firm* — Wentsler LLC

(57) ABSTRACT

Aspects of the present disclosure provide a delivery device including a tubular outer jacket having a distal end and a tyne assembly including a shaft supporting at least one tyne. In some aspects, an inner jacket is positioned within the outer jacket, wherein the tyne assembly is positioned between the outer jacket and the inner jacket. The delivery device has a delivery configuration in which the tynes are maintained within the outer jacket and a deployed configuration in which the tynes extend from a distal end of the tubular outer jacket. Aspects of the disclosure also provide methods of conducting a percutaneous coronary intervention including utilizing one or more tyne assemblies to engage the tynes of each tyne assembly with the frame to maintain the position of the delivery device.

7 Claims, 12 Drawing Sheets

(58) Field of Classification Search
CPC ........... A61B 2017/00349; A61B 2017/22038; A61B 2017/0287
See application file for complete search history.

(56) References Cited

U.S. PATENT DOCUMENTS

| | | | | |
|---|---|---|---|---|
| 7,789,876 | B2 * | 9/2010 | Zikorus | A61B 18/1492 600/478 |
| 9,586,024 | B2 | 3/2017 | Coates | |
| 2002/0068866 | A1 | 6/2002 | Zikorus et al. | |
| 2002/0161377 | A1 | 10/2002 | Rabkin | |
| 2003/0114901 | A1 | 6/2003 | Loeb et al. | |
| 2004/0111143 | A1 | 6/2004 | Fischell et al. | |
| 2012/0277853 | A1 | 11/2012 | Rothstein | |
| 2014/0277366 | A1 * | 9/2014 | Cummins | A61F 2/966 623/1.12 |
| 2017/0056215 | A1 | 3/2017 | Nagesh et al. | |
| 2018/0014957 | A1 | 1/2018 | Harris et al. | |
| 2019/0192290 | A1 | 6/2019 | Pfenniger et al. | |
| 2019/0298991 | A1 | 10/2019 | Bomzin et al. | |

FOREIGN PATENT DOCUMENTS

| | | | | |
|---|---|---|---|---|
| EP | 3501453 | | 6/2019 | |
| WO | WO-2007027830 | A1 * | 3/2007 | A61M 27/002 |
| WO | 2017091605 | | 6/2017 | |

* cited by examiner

TYNE DOCKING FOR PERCUTANEOUS CORONARY INTERVENTION ACCESS

CROSS-REFERENCE TO RELATED APPLICATIONS

This is the National Stage under 35 U.S.C. § 371 of International Application No. PCT/US2021/023554, filed Mar. 23, 2021, which claims the benefit of U.S. Provisional Patent Application No. 62/993,383, filed Mar. 23, 2020, the entire content of which is incorporated herein by reference.

FIELD

The present technology is generally related to delivery devices for and methods of docking the delivery device to an implanted prosthetic heart valve to assist in percutaneous coronary intervention procedures.

BACKGROUND

Diseased or otherwise deficient heart valves can be repaired or replaced with an implanted prosthetic heart valve. Conventionally, heart valve replacement surgery is an open-heart procedure conducted under general anesthesia, during which the heart is stopped and blood flow is controlled by a heart-lung bypass machine. Traditional open surgery inflicts significant patient trauma and discomfort, and exposes the patient to a number of potential risks, such as infection, stroke, renal failure, and adverse effects associated with the use of the heart-lung bypass machine, for example.

Due to the drawbacks of open-heart surgical procedures, there has been an increased interest in minimally invasive and percutaneous replacement of cardiac valves. With percutaneous transcatheter (or transluminal) techniques, a prosthetic heart valve is compacted for delivery in a catheter and then advanced, for example, through an opening in the femoral artery and through the descending aorta to the heart, where the prosthetic heart valve is then deployed in the annulus of the valve to be restored (e.g., the aortic valve annulus). Although transcatheter techniques have attained widespread acceptance with respect to the delivery of conventional stents to restore vessel patency, only mixed results have been realized with percutaneous delivery of the more complex prosthetic heart valve.

The presence of the prosthetic heart valve can make percutaneous coronary interventions difficult as the accessing various locations in the heart, such as the coronary ostium, which may be at least partially obstructed by the prosthetic heart valve.

SUMMARY

The techniques of this disclosure generally relate to delivery devices that can engage or be "docked" to a previously implanted prosthetic heart valve to maintain the position of the delivery device during a percutaneous coronary intervention.

In one aspect, the present disclosure provides a delivery device including a tubular outer jacket having a distal end and a tyne assembly including a shaft supporting a tyne. The delivery device further includes an inner jacket positioned within the outer jacket, wherein the tyne assembly is positioned between the outer jacket and the inner jacket. The delivery device has a delivery configuration in which the tyne is maintained within the outer jacket and a deployed configuration in which the tyne extends from a distal end of the outer jacket.

In another aspect, the disclosure provides a method of conducting a percutaneous coronary intervention. The method includes providing a delivery device having a tubular outer jacket having a distal end and a tyne assembly including a shaft supporting a tyne; wherein the delivery device is in a delivery configuration in which the tyne is maintained within the outer jacket. The method includes directing a distal end of the delivery device to an implanted prosthetic heart valve, the prosthetic heart valve including a frame defining a plurality of cells. The tyne assembly is then distally advanced at least partially through one of the plurality of cells to engage the tyne with the frame at a position distal with respect to the distal end.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Specific embodiments of the present disclosure are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. Although the present disclosure has been described with reference to preferred embodiments, workers skilled in the art will recognize that changes can be made in form and detail without departing from the spirit and scope of the present disclosure.

Figure 1:
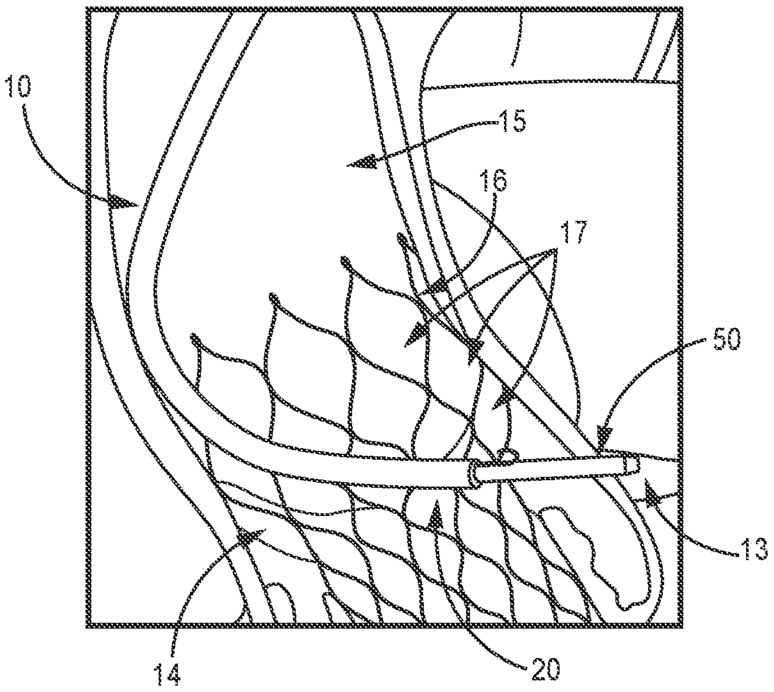
FIG. 1 is a schematic illustration of a delivery device operatively positioned through an implanted prosthetic heart valve and within an ostia for the delivery of a treatment device to the ostia.

One example of a delivery device 10 for delivering a treatment device for percutaneous coronary intervention is collectively illustrated in FIGS. 1-6I. The delivery device 10 can be used to deliver a treatment device 12 (only visible in FIG. 6I) including, but not limited to, a stent, angioplasty device, deburring device or any other device used for percutaneous coronary intervention that can be delivered via catheter. In general terms and as is shown in FIG. 1, the delivery device 10 is configured to be delivered to a treatment site 13 located proximate a previously implanted prosthetic heart valve 14. The delivery device 10 is configured to engage or be docked to a frame 16 of the prosthetic heart valve 14 to maintain the position of the delivery device 10 as the treatment device 12 is delivered through the delivery device 10 to the treatment site 13 and also during treatment. The frame 16 includes a plurality of cells 17 (only a few of which are referenced for ease of illustration) and the delivery device 10 can be docked to one or more adjacent cells 17. Therefore, it is believed that use of the delivery device 10 increases clinician ease in delivering the treatment device and lowers the skill required to do so. Embodiments of the disclosure also assist in steering both the delivery device 10 and the treatment device 12.

In one embodiment, the delivery device 10 includes a tubular outer jacket 20 having a body 22 defining a lumen 24 terminating at a distal opening 26. The outer jacket 20 may be made of one or more polymers, such as polyether block amides or the like. A tyne assembly 30 (FIG. 2B) is coaxially positioned within the lumen 24 and can slide therein. In one example, the tyne assembly 30 includes a shaft 32 and at least one tyne 34 extending from the shaft 32. The shaft 32 can take a variety of configurations and may be tubular or nontubular. The tyne assembly 30 is configured to have a delivery configuration in which each tyne 34 is compressed and flattened to fit within the lumen 24 of the outer jacket 20. In one example, each tyne 34 may be linear in the delivery configuration. The tyne assembly 30 can be distally advanced out the distal opening 26 of the outer jacket 20 so that each tyne 34 extends at least partially out of the distal opening 26 and is generally freed from the compressive forces of the outer jacket 20 or any other components provided within the outer jacket 20 in which the tyne(s) 34 are located. In the deployed configuration, shown in FIG. 2A, each tyne 34 transitions to its natural arrangement.

Figure 5A:
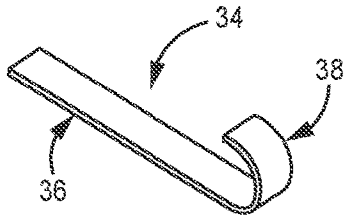
FIGS. 5A-5C illustrate an example of a tyne of the device of FIGS. 1-3.
Figure 5B:
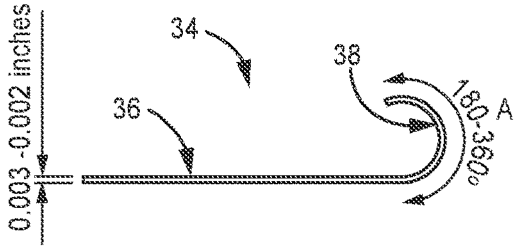
Figure 5C:
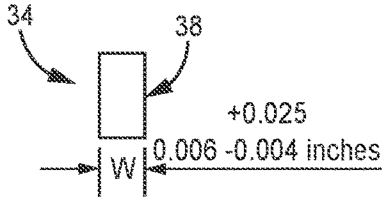

Referring now in particular to FIGS. 5A-5C, which illustrate an example of a suitable tyne 34 in detail in its natural arrangement. In this example, the tyne 34 includes an end portion 36 connected to a hook 38. In one embodiment, the tyne 34 is made of a material having a thickness T between 0.003-0.007 inches. In another embodiment, the thickness T is between 0.003-0.002 inches. In one example, the tyne 34 has a width W of 0.006-0.029 inches. In another example, the width W is between 0.006-0.004 inches. In one embodiment, the hook 38 defines an arc A spanning between 180-360 degrees. Therefore, in one embodiment, the hook 38 forms a loop spanning a full circle, 360 degrees in its natural arrangement. In yet another embodiment, the hook may span substantially 360 degrees (i.e. 330 degrees or more) in its natural arrangement. The tyne 34 can be made of one or more shape-memory materials, such as one or more shape-memory alloys including nitinol, and/or one or more shape-memory polymers. The end portion 36 can be connected to shaft 32, or otherwise, shaft 32 and end portion 36 can be integrally or seamlessly constructed. In one embodiment, tyne assembly 30 does not include a shaft 32 but instead includes one or more longitudinally extending tynes 34 extending from end portion 36 to handle assembly 70 (see FIG. 2C).

Figure 2A:
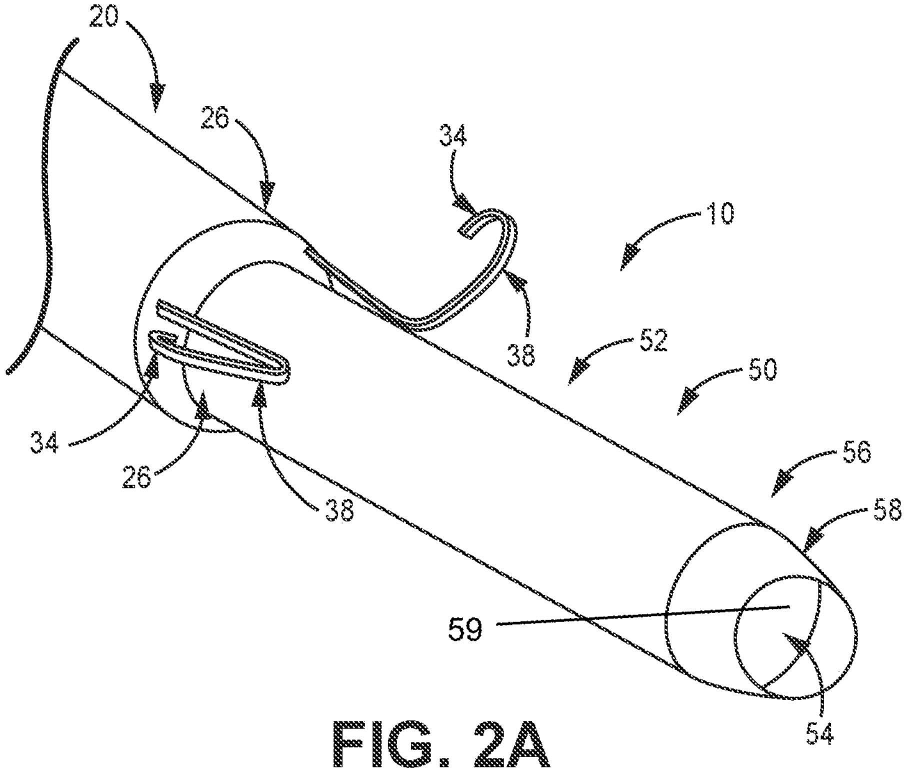
FIG. 2A is a partial, perspective view of the delivery device of FIG. 1.
Figure 2B:
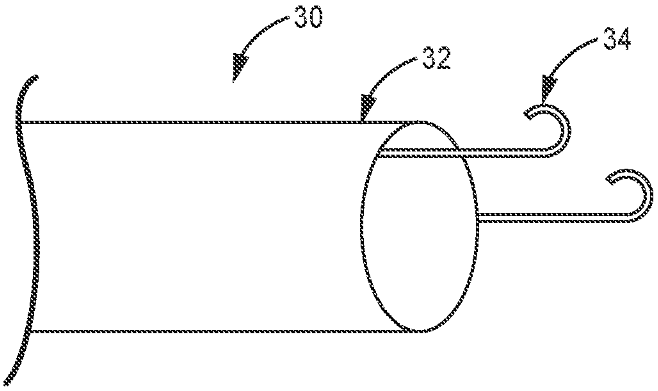
FIG. 2B is a partial, perspective view of a tyne assembly of the delivery device of FIG. 2A.
Figure 2C:
FIG. 2C is a perspective view of an alternate tyne assembly that can be used with the delivery devices disclosed herein.
Figure 2D:
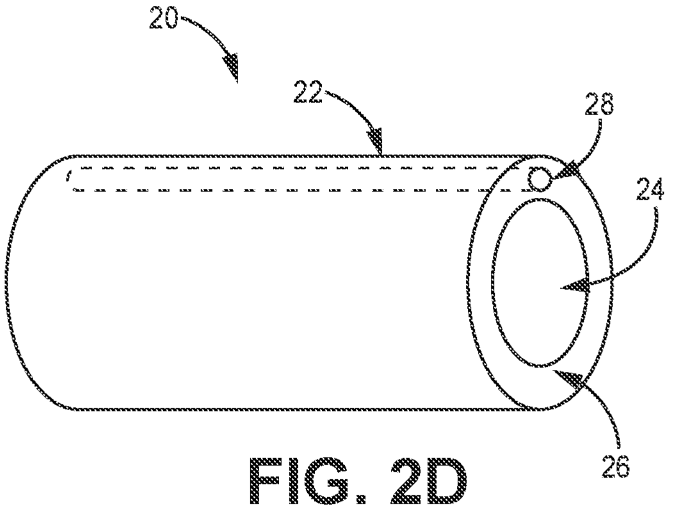
FIG. 2D is a partial, perspective view of an outer jacket of the delivery device of FIG. 1.
Figures 2E, 2F, 2G:
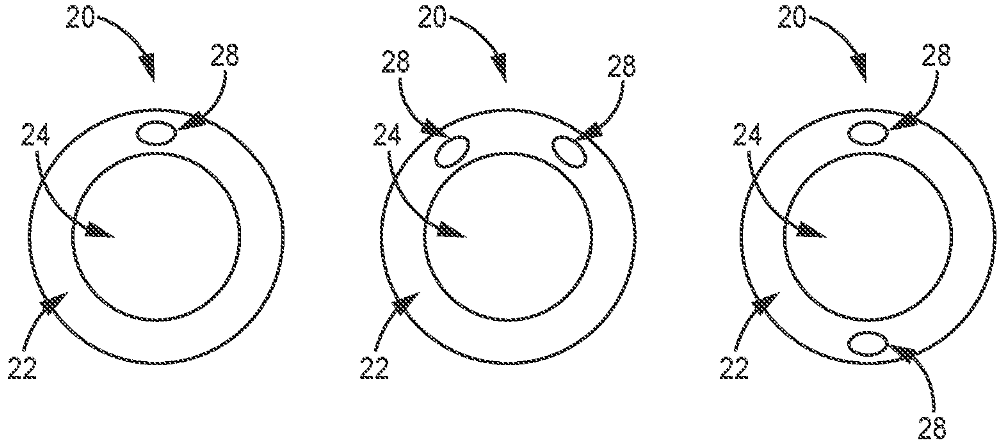
FIGS. 2E-2I illustrate alternate lumen configurations for the outer jacket of FIGS. 1 and 2A-2D.
Figure 2H:
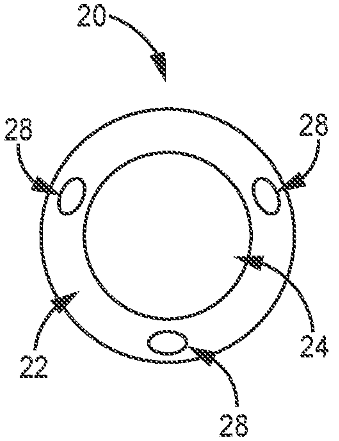
Figure 2I:
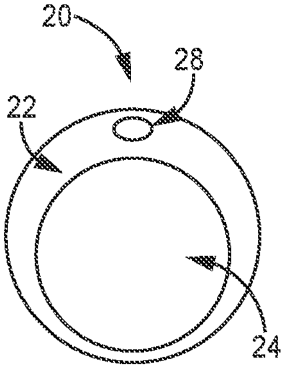
Figure 2J:
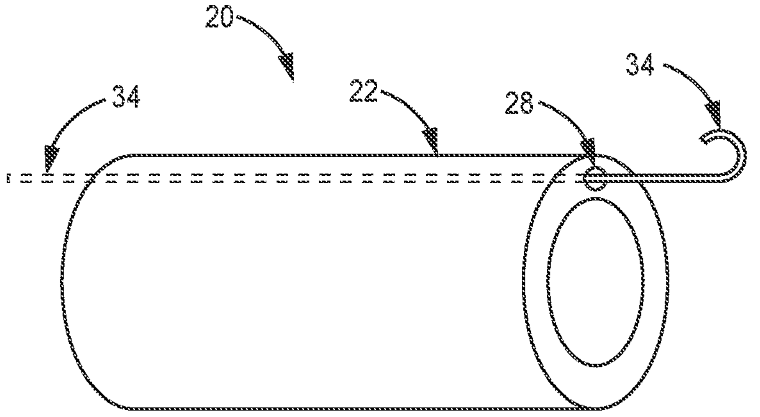
FIG. 2J illustrates an outer jacket, similar to that of FIG. 2E, including a single tyne coaxially positioned within a single lumen.
Figure 2K:
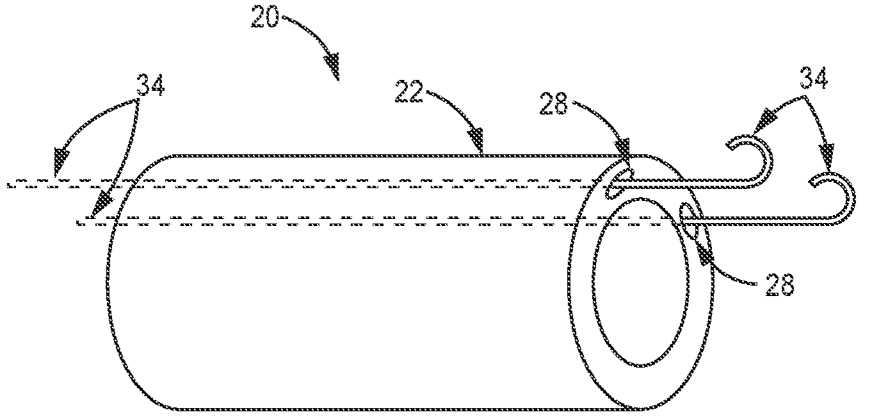
FIG. 2K illustrates an outer jacket, similar to that of FIG. 2F, including two tynes extending within respective lumens.
Figure 3:
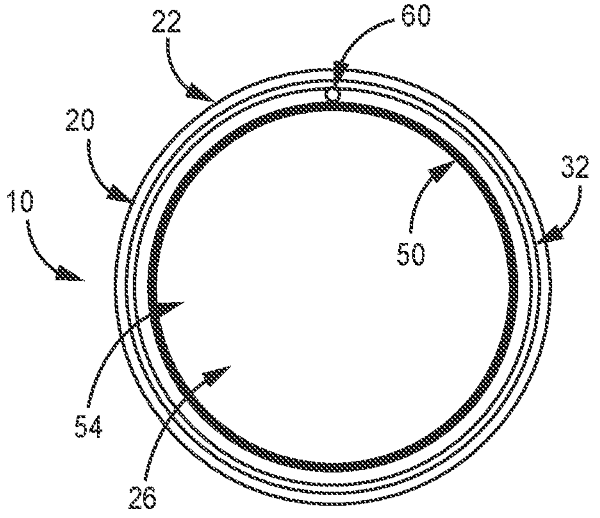
FIG. 3 is a cross-sectional view of the delivery device of FIGS. 1-2.
Figure 4A:
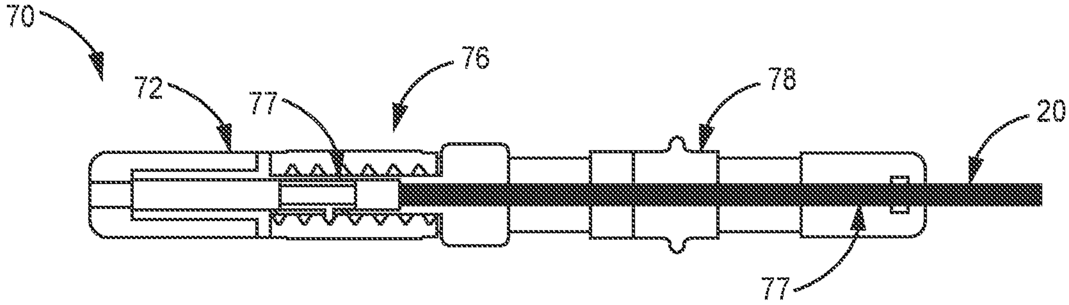
FIG. 4A-4D are cross-sectional views of a handle assembly that can be used with the delivery device of FIGS. 1-3.
Figure 4B:
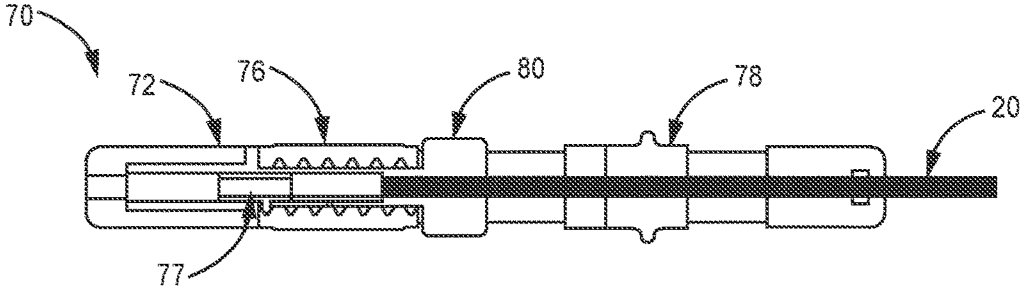
Figure 4C:
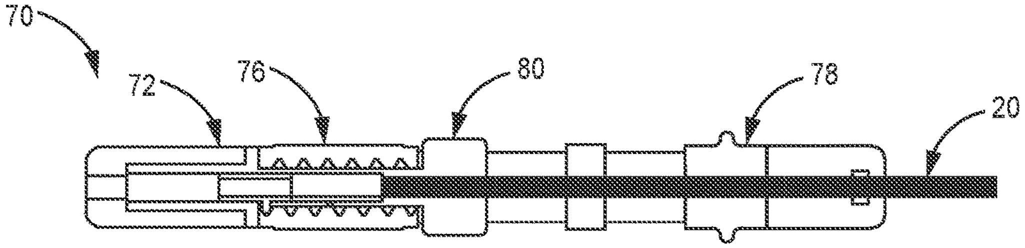
Figure 4D:
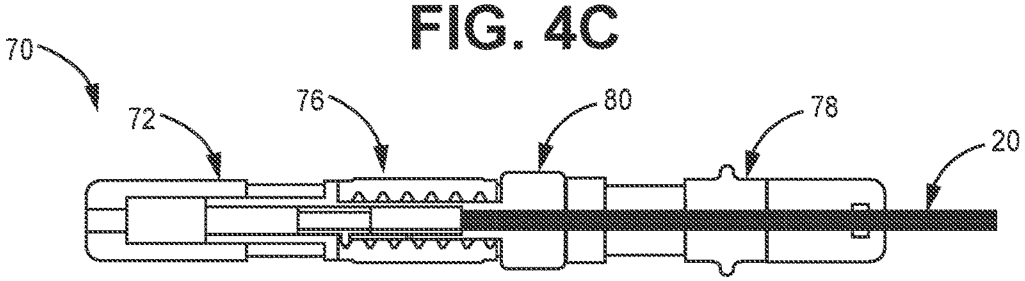

In one embodiment, the tubular outer jacket 20 having a body 22 defining a lumen 24 terminating at a distal opening 26 includes one or more lumens 28 extending the entire length of tubular outer jacket 20 (see FIG. 2D) and wherein tyne 34 is coaxially positioned within a lumen 28 and can slide therein. FIG. 2E shows a cross section of a tubular outer jacket 20 including one lumen 28 whereas FIG. 2F shows a cross section of a tubular outer jacket 20 including two lumens 28. In some embodiments tubular outer jacket 20 can include two or more lumens 28 spaced circumferentially around the circumference of body 22 (see, e.g., FIGS. 2F-2H). In various embodiments, lumen 24 can be offset within body 22 of outer tubular jacket 20 wherein the wall thickness of body 22 can vary around the circumference of lumen 24 (see FIG. 2I). FIG. 2J shows the tubular outer jacket 20 including a single tyne 34 coaxially positioned within a single lumen 28. FIG. 2K shows tubular outer jacket 20 including two tynes 34 coaxially positioned within two lumens 28. The outer jackets 20 and lumen(s) 28 of FIGS. 1-6I, and are identically configured except as explicitly stated herein. Similarly, the tyne assemblies 30 and tynes 34 of FIGS. 1-6I are identically configured except as explicitly stated herein.

Optionally, the delivery device 10 can further include an inner jacket 50 positioned within both the outer jacket 20 and the tyne assembly 30. The inner jacket 50 includes a body 52 defining a lumen 54 terminating at a distal end 56 so that the treatment device 12 can be delivered therethrough. In some embodiments, the distal end has a hollow tip 58. In one example, the tip 58 is tapered. In one example, the tip 58 is made of a material that is more flexible with respect to the body 52. Where provided, the inner jacket 50 can be distally advanced from a position within the outer jacket 20 (a delivery configuration) to a position proximally past the distal opening 26 of the outer jacket 20 as is shown in FIG. 2. In various embodiments, an inner surface of the inner jacket 50 includes a liner 59. The liner 59 can be made of a low-friction material such as polytetrafluoroethylene ("PTFE") or ePTFE so that the liner 59 has a coefficient of friction in a range of 0.05-0.10, for example. The liner 59 can also be applied to the outer jacket 20 if the inner jacket 50 is not provided.

To steer or direct the delivery device 10 as it is being advanced through a patient's vasculature, the delivery device 10 can include a pull wire 60. In one example, the pull wire 60 is embedded within or connected to the inner jacket 50 in such a way that the pull wire 60 cannot move longitudinally with respect to the inner jacket 50. In an alternate embodiment, the inner jacket 50 can include an external channel in which the pull wire 60 is secured. As the pull wire 60 is tensioned (i.e. pulled proximally), the inner jacket 50 will bend, thus also bending the flexible outer jacket 20 and effectively steering the delivery device 10 as desired. In one example, the pull wire 60 is made of stainless steel or the like. In an alternative embodiment, the pull wire 60 can be incorporated into the outer jacket 20. Other known methods of steering a catheter can also be applied to steering the inner or outer jackets 20, 50, as desired.

Various embodiments include a handle assembly 70 to maintain and/or actuate movement of the outer jacket 20, tyne assembly 30, inner jacket 50 and pull wire 60. One example of a suitable handle assembly 70 is illustrated in FIGS. 4A-4D. In this example, the handle assembly 70 includes a body 72 defining a lumen 74 in which the outer jacket 20 is fixedly maintained. The handle assembly 70 includes a first actuator 76 connected to the pull wire 60 and configured to rotate about the body 72 to correspondingly pull the pull wire 60, which is connected at pull wire interface 77, to steer the delivery device 10. The handle assembly 70 further includes a second actuator 78 connected to the tyne assembly 30 that can slide longitudinally from a first position (FIGS. 4A-4B) to a second position (FIGS. 4C-4D) to correspondingly slide the tyne assembly 30 proximally or distally with respect to the outer jacket 20 to retract or extend the tyne(s) 34 from the distal opening 26 of the outer jacket 20, respectively. If the inner jacket 50 is provided, the handle assembly 70 can also include a third actuator 80 connected to the inner jacket 50. In one example, when the third actuator 80 is slidably connected to the body 72, the third actuator 80 longitudinally transitions (i.e. slides) from a first position (FIGS. 4A-4C) to a second position (FIG. 4D) in to move the inner jacket 50 from a position entirely within the outer jacket 20 to at least partially extending out of the distal opening 26 of the outer jacket 20.

Figure 6A:
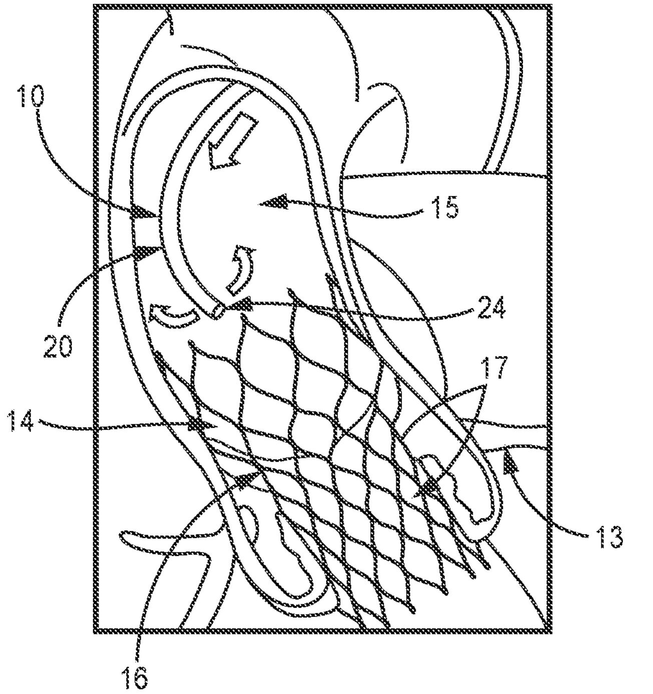
FIGS. 6A-6I illustrate a method of delivery a treatment device with the delivery device of FIGS. 1-3.
Figure 6B:
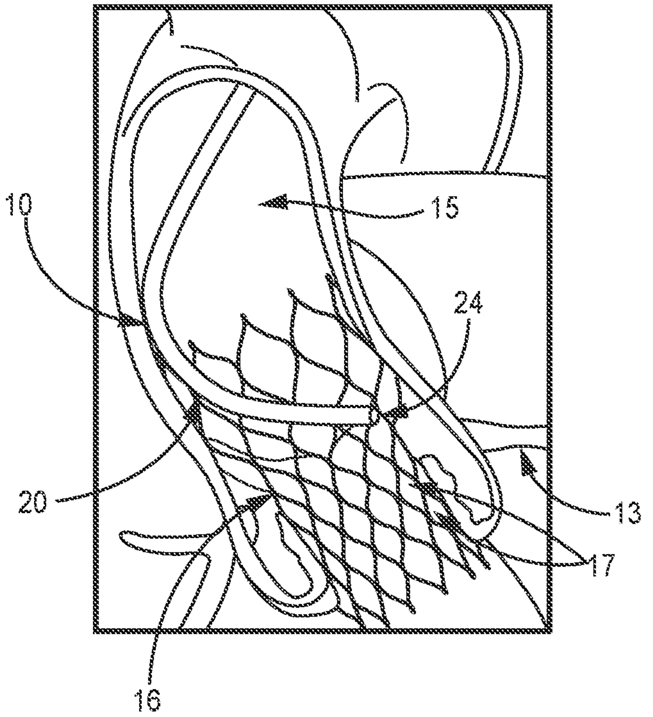
Figure 6C:
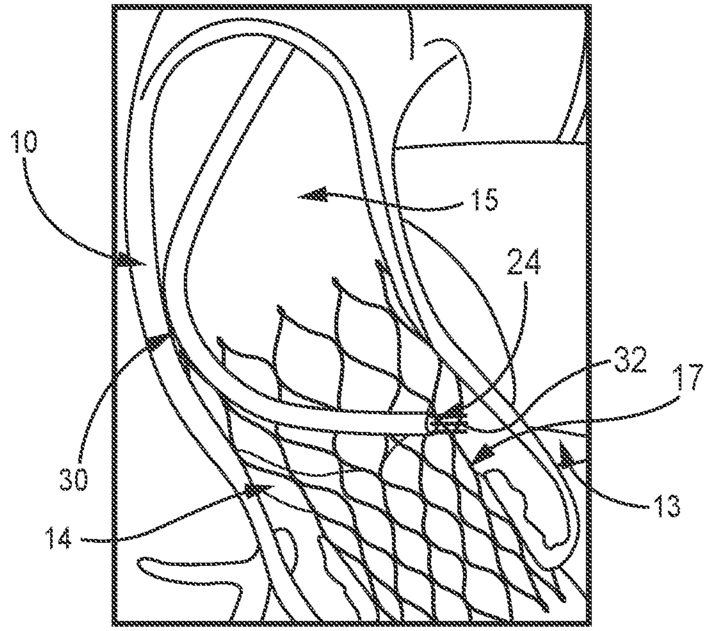
Figure 6D:
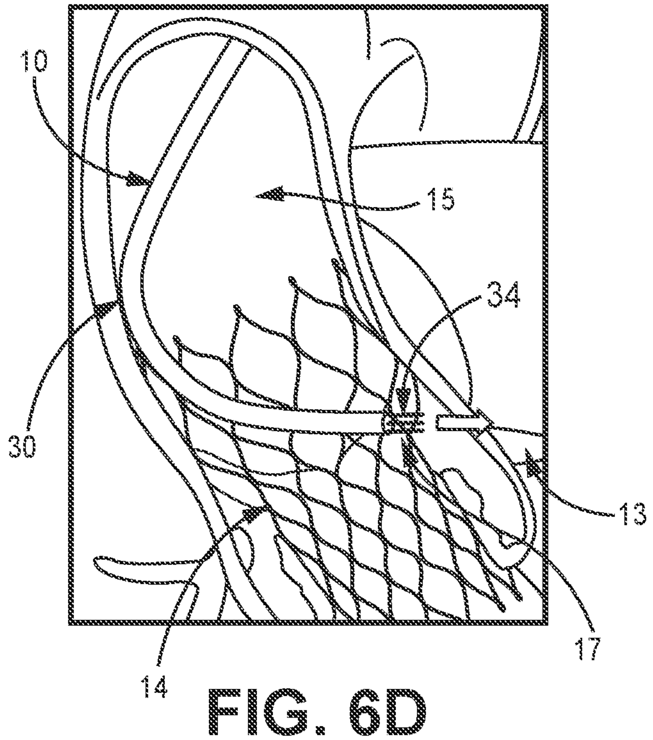
Figure 6E:
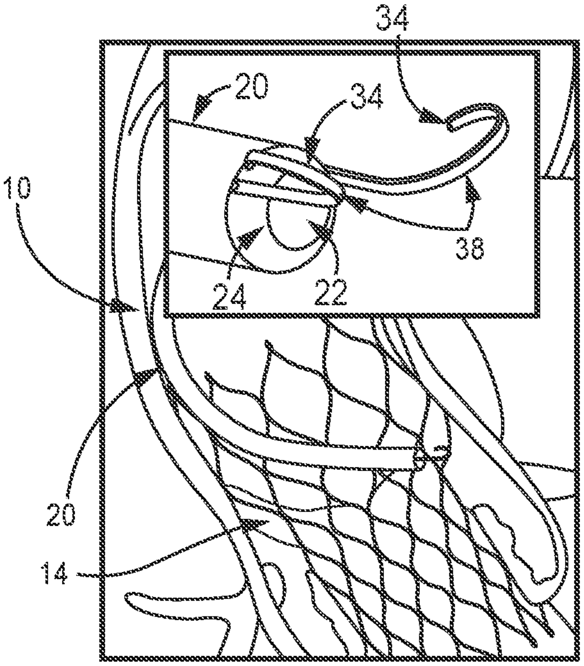
Figure 6F:
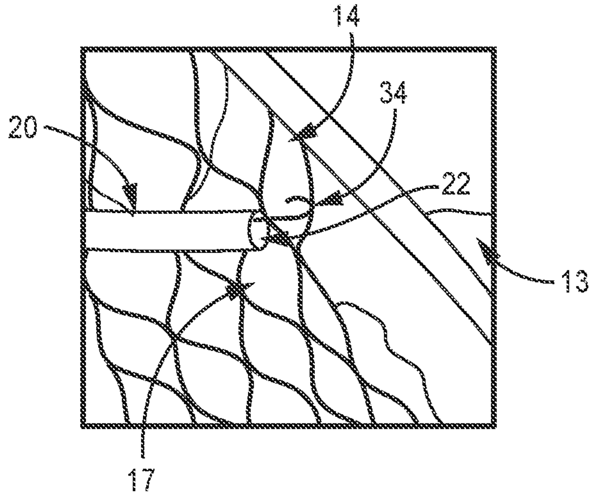
Figure 6G:
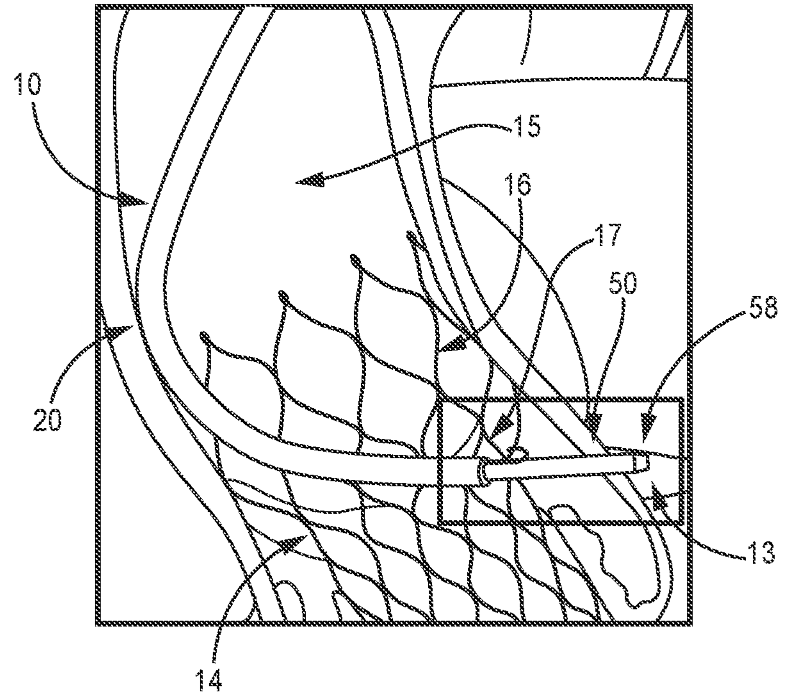
Figure 6H:
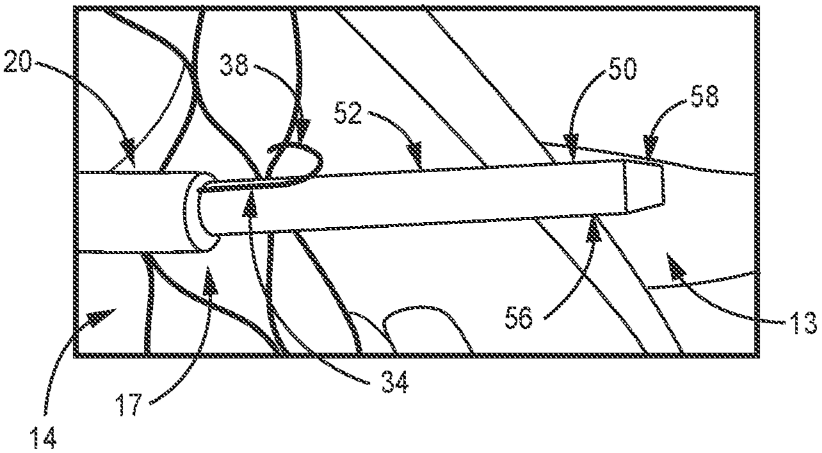

Referring in addition to FIGS. 6A-6I, which illustrate example methods of using the delivery devices of the disclosure. In one such method, the delivery device 10 is used to position the treatment device 12 (schematically represented in FIG. 6I) to the treatment site 13 (e.g., a coronary ostia) in a patient who has a previously implanted aortic prosthetic heart valve 14. As shown in FIG. 7A, the delivery device 10 can be guided to an aorta 15 in a delivery configuration (i.e. having the tyne assembly 30 and optional inner jacket 50 positioned entirely within, proximally to the distal opening 26 of the outer jacket 20). Optionally, the pull wire 60 can be used to steer the distal end of the outer jacket 20, as desired to locate the distal opening 26 of the outer jacket 20 through one cell 17 that is adjacent or in the vicinity of coronary access (i.e. proximate the treatment site 13; FIG. 6B) as can be confirmed via fluoroscopy using known techniques. In this position, the distal opening 26 of the outer jacket 20 will be proximate the frame 16 of the previously implanted prosthetic heart valve 14. Then, the tyne assembly 30 is distally advanced within the lumen 24 of the outer jacket 20 so that the tyne(s) 34 (generally referenced) partially extend out of the distal opening 26 of the outer jacket 20, through one cell 17 in the frame 16. Then, it can be confirmed that placement of the delivery device 10 is in the desired cell 17 (the cell 17 illustrated is merely one example). Once confirmed, the tyne assembly 30 can be further distally advanced so that each tyne 34 fully transitions to the deployed arrangement. As each tyne 34 is configured to curl proximally, each tyne 34 will engage the frame 16, thus docking the delivery device 10 to the frame 16 at a position distal with respect to the distal end 26 of the outer member 20. In other words, the tynes 34 will lock the position of the delivery device 10 with respect to both the frame 16 and the treatment site 13. Engagement of each tyne 34 to the frame 16 can be confirmed by tugging the tyne assembly 30 proximally to sense engagement. Once the delivery device 10 is engaged, a treatment device 12 can be guided through the lumen of the outer jacket 20 (via the lumen 54 of the inner jacket 50, if provided) to the distal opening 26 of the outer jacket 20. If desired and if provided, the inner jacket 50 can be distally advanced through the lumen 24 of the outer jacket 20 once the tyne(s) 34 are engaged to the frame 16 as is shown in FIGS. 6G-6H. In one example, the inner jacket 50 is distally advanced into the treatment site 13 (e.g., the ostia) as is also shown in FIGS. 6G-6H prior to delivery of the treatment device 12.

The aforementioned technique effectively locks the delivery device to the stent frame. It has been observed that sometimes, once the physician gets the catheter in position and finds an appropriate cell as close as they can get to the ostia, when trying to advance the catheter into the ostia, the catheter slips out of the cell. Sometimes when the physician finds the right cell they can advance straight into the ostia, but sometimes it is a challenge.

Figure 6I:
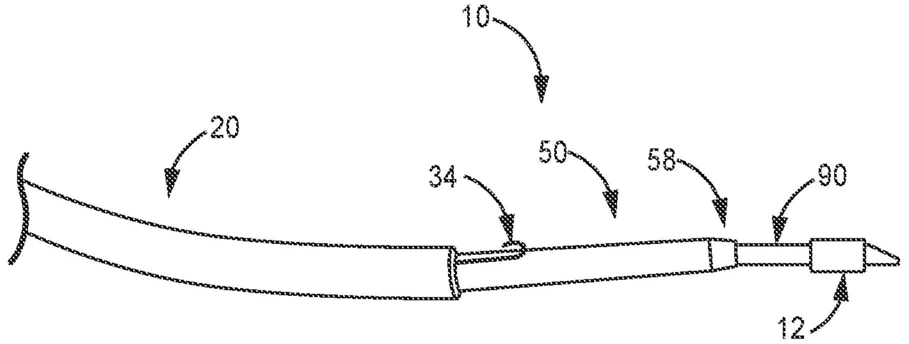
Figure 7A:
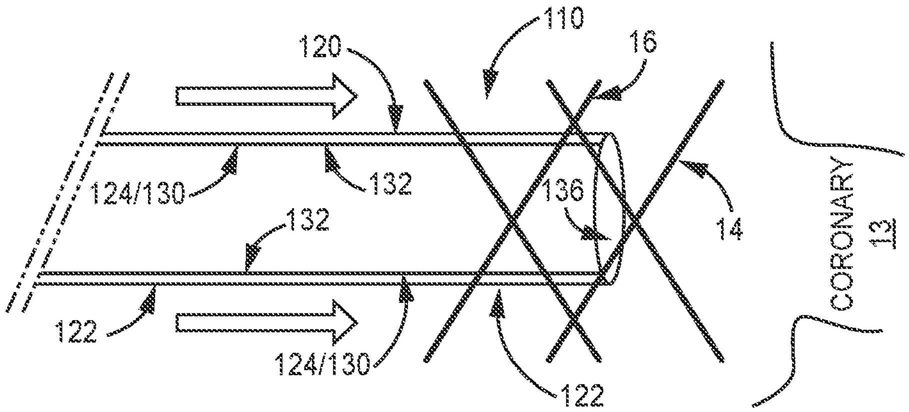
FIG. 7A schematically illustrates a delivery device including an outer jacket having independent lumens through which respective tyne assemblies can be delivered in an uncurled configuration.

FIG. 6I illustrates delivery of the treatment device 12 via a delivery catheter 90 that is inserted through the inner jacket 50 or, alternatively through the outer jacket 20 if an inner jacket is not provided.

Figure 7B:
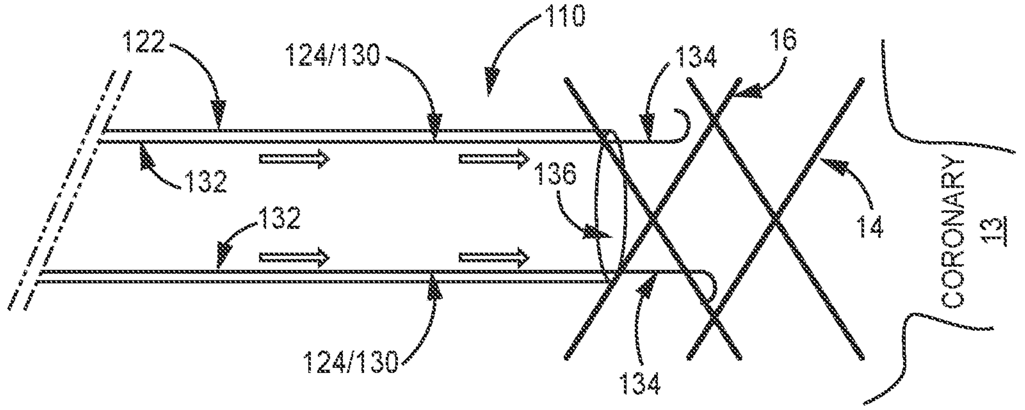
FIG. 7B schematically illustrates two tyne assemblies of the delivery device of FIG. 7A having been pushed out of a distal end of the outer jacket so that tynes of the tyne assemblies can transition to a curled configuration.

Referring now in addition to FIGS. 7A-7B, which schematically illustrate select portions of yet another delivery device 110 that can be used similar to other delivery devices disclosed herein except as expressly stated. In this example, the delivery device 110 includes an outer jacket 120 having a tubular body 122. The body 122 includes a plurality of lumens 124 formed within the body 122. In one example, two lumens 124 are provided within the body 122 and are positioned approximately 180 degrees from each other (+/−5 degrees). Each lumen 124 is sized to slidably receive a tyne assembly 130. In one example, the tyne assembly 130 is an elongated wire or the like. In one example, each tyne assembly 130 includes a proximal or shaft portion 132 and a tyne 134 at its distal end. The shaft portion 132 and tyne 134 can be homogenously formed so that the tyne assembly 130 generally resembles a wire. Each tyne 134 is configured to be delivered in an arrangement (FIG. 7A) that is uncurled with respect to the shaft or proximal portion of the tyne 134, entirely within the respective lumen 124. Each tyne 134 can further take a curled configuration (FIG. 7B) to engage the stent frame 16 of the prosthesis 14 proximate a distal opening 136 of the outer jacket 120. In one example, each tyne 134 can be made of a shape memory material that is configured to curl upon release from the constraint of the body 122. In another example, dielectric current may be applied to selectively curl each tyne 134 when the tyne 132 is distally advanced past the distal end 136 so that it is freed from the body 122.

Figure 8A:
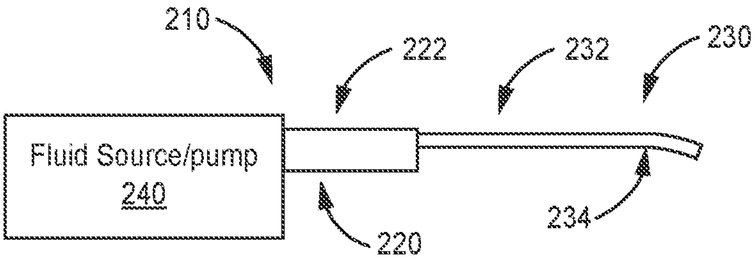
FIGS. 8A-8B schematically illustrate a distal end of a delivery device having an outer jacket through which a tyne assembly can be positioned, wherein the tyne assembly transitions from the position of FIG. 8A to the position of FIG. 8B via removal of fluid inflating the tyne assembly.
Figure 8B:
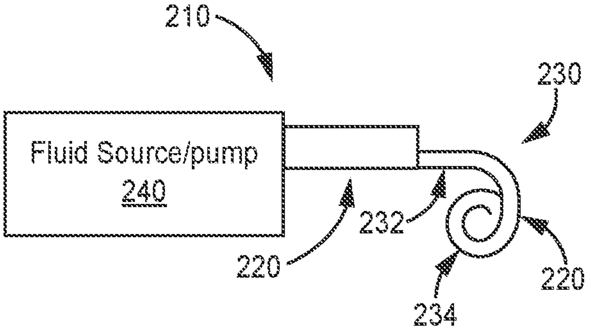
Figure 9:
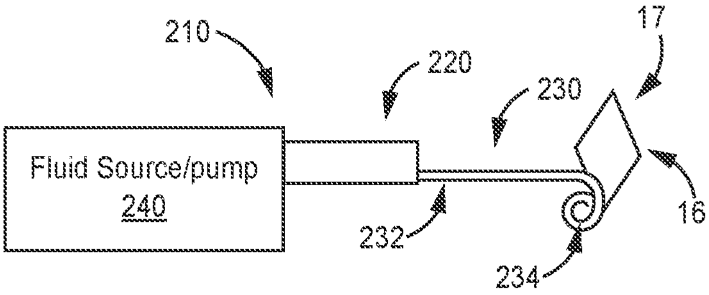
FIG. 9 is a schematic illustration of the tyne assembly of FIGS. 8A-8B engaging a cell of a frame of a prosthesis.

Referring now in addition to FIGS. 8A-9, which schematically illustrate yet another delivery device 210 that can be used similar to other delivery devices disclosed herein except as expressly stated. In this example, the delivery device 210 includes an outer jacket 220 having a tubular body 222. The body 222 defines a lumen (not visible) formed within the body 222. The lumen is sized to slidably receive a tyne assembly 230 similar to embodiments disclosed above. In one example, the tyne assembly 230 is formed of flexible material having a cavity formed along its length, which is connected to a source of pressurized fluid 240 (e.g., gas, liquid). Each tyne assembly 230 includes a proximal portion 232 and a tyne 234 at its distal end, the tyne 234 configured to curl (FIG. 8B) when fluid from the fluid source is substantially removed. The tyne 234 is configured to be delivered in an arrangement that is uncurled with respect to the proximal portion 232 of the tyne assembly 230. Therefore, in the delivery arrangement, fluid is introduced into the cavity to fill the cavity and force the tyne 234 to straighten. In an alternate embodiment, the tyne assembly 230 can be substantially void of fluid and collapsed within the lumen for delivery. The tyne 234 can be distally advanced out of the outer jacket 220 and then inflated to the position of FIG. 8A so that the tyne 234 can be inserted through the stent frame 16. Once the tyne 234 is inserted through a cell 17 of a stent frame 16, the fluid can be substantially removed from the cavity via the fluid source/pump 240 to an extent where the tyne 234 transitions to its curled arrangement, engaging the stent frame 16 as is shown in FIG. 9. In one example, the curled arrangement is one in which the tyne 234 revolves over 360 degrees. In one example, the curled arrangement is one in which the tyne revolves 450 degrees or more.

As previously stated, the treatment device 12 is schematically represented and can be any of the type delivered via a catheter for a coronary intervention procedure. The methods of the disclosure thus can include the delivery and use of any such treatment devices 12 in manners known with respect to such treatment devices. To name a few examples, the treatment device 12 can be a stent, angioplasty device, deburring device.

It is also to be understood that the prosthetic heart valve 14 shown is provided as an illustrative example and that the present disclosure is not intended to be limited to any particular prosthetic heart valve, frame 16 or cell 17 design.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A delivery device comprising:

a tubular outer jacket having a distal end, the outer jacket comprising a lumen disposed between an inner surface and an outer surface of the outer jacket; and a tyne assembly including a shaft supporting a tyne configured to grasp onto a stent frame wire, the tyne assembly positioned in the lumen of the outer jacket;

an inner jacket positioned within the outer jacket;

wherein the delivery device is movable between:

a delivery configuration in which a distal end of the tyne and a distal end of the inner jacket are maintained within the outer jacket, a first deployed configuration in which a portion of the tyne is maintained within the outer jacket, and the distal end of the tyne extends from a distal end of the outer jacket and axially beyond a distal end of the inner jacket, and a second deployed configuration wherein the portion of the tyne is maintained within the outer jacket, the distal end of the tyne extends from the distal end of the outer jacket, and the distal end of the inner jacket extends from the distal end of the outer jacket and axially beyond the distal end of the tyne.

2. The delivery device of claim 1, wherein the inner jacket includes a body having a distal end having a tip proximate the distal end; wherein the tip is tapered and is more flexible than the body.

3. The delivery device of claim 1, wherein the tyne assembly further comprises a second tyne, wherein the second tyne is positioned in a second lumen disposed between the inner surface of the outer jacket and the outer surface of the outer jacket.

4. The delivery device of claim 1, wherein the tyne includes a hook shaped in an arc in a range of 180 to 360 degrees.

5. The delivery device of claim 1, wherein the tyne includes a hook having a width in a range of 0.006-0.029 inches.

6. The delivery device of claim 1, further comprising a pull wire configured to steer the delivery device.

7. The delivery device of claim 1, further comprising a liner applied to the inner jacket.

* * * * *